US006667423B2

(12) United States Patent
Dumonteil et al.

(10) Patent No.: US 6,667,423 B2
(45) Date of Patent: *Dec. 23, 2003

(54) PROCESS FOR THE PRODUCTION OF A DIENE IN THREE SUCCESSIVE STAGES FROM A TERTIARY ALKYL ETHER

(75) Inventors: Claire Dumonteil, Bron (FR); Alain Forestiere, Vernaison (FR); Marie-Claire Marion, Villeurbanne (FR)

(73) Assignee: Institut Francais du Petrole, Rueil Malmaison (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/392,571

(22) Filed: Sep. 9, 1999

(65) Prior Publication Data

US 2003/0114725 A1 Jun. 19, 2003

(30) Foreign Application Priority Data

Sep. 9, 1998 (FR) .............................................. 98 11285

(51) Int. Cl.[7] .......................... C07C 1/207; C07C 1/213
(52) U.S. Cl. ....................... 585/603; 585/601; 585/606; 585/607; 585/608; 585/609; 585/616; 585/617
(58) Field of Search ................................. 585/601, 603, 585/606, 607, 608, 609, 616, 617, 639, 658, 506

(56) References Cited

U.S. PATENT DOCUMENTS

| 3,270,081 | A | | 8/1966 | Verdol et al. ............... 260/681 |
|---|---|---|---|---|
| 3,927,138 | A | * | 12/1975 | Walker .................. 260/680 E |
| 4,108,918 | A | * | 8/1978 | Hoppstock et al. ......... 585/624 |
| 4,447,668 | A | | 5/1984 | Smith, Jr. et al. |
| 4,656,016 | A | | 4/1987 | Taramasso et al. |
| 5,095,164 | A | | 3/1992 | Gabel et al. |
| 5,354,831 | A | | 10/1994 | Panster et al. |
| 5,567,860 | A | | 10/1996 | Mowry et al. |
| 5,994,594 | A | * | 11/1999 | Marion et al. .............. 568/579 |
| 6,028,239 | A | * | 2/2000 | Marion et al. .............. 585/640 |
| 6,049,020 | A | * | 4/2000 | Marion et al. .............. 585/639 |
| 6,100,438 | A | * | 8/2000 | Marion et al. .............. 585/639 |

FOREIGN PATENT DOCUMENTS

| DE | 3509292 | 12/1985 |
|---|---|---|
| EP | 0 860 412 | 8/1998 |
| EP | 0869107 A1 | 10/1998 |
| EP | 0869108 A1 | 10/1998 |
| FR | 2527201 | 11/1983 |
| FR | 2 747 120 | 10/1997 |
| GB | 2188853 | 10/1987 |

* cited by examiner

Primary Examiner—Thuan D. Dang
(74) Attorney, Agent, or Firm—Millen, White, Zelano & Branigan, P.C.

(57) ABSTRACT

For the production of a diene a process in three stages comprises a stage a) for decomposition of at least one tertiary alkyl ether in a mixture that contains at least one tertiary olefin, at least one alcohol and at least one residual ether, in the presence of a catalyst that comprises at least one mineral solid that is grafted by at least one organic group such as alkyl sulfonic acid, sulfonic aryl and/or sulfonic alkylaryl, a stage b) for purification of the olefin that is obtained in stage a), and a stage c) for oxidizing dehydrogenation of the tertiary olefin that is obtained in stage b) in the presence of a catalyst under conditions for obtaining a diene.

34 Claims, No Drawings

PROCESS FOR THE PRODUCTION OF A DIENE IN THREE SUCCESSIVE STAGES FROM A TERTIARY ALKYL ETHER

FIELD OF THE INVENTION

The invention relates to a process for the production of a diene that comprises a stage a) for decomposition of at least one tertiary alkyl ether into at least one tertiary olefin of high purity, a stage b) for purification of the tertiary olefin and a stage c) for oxidizing dehydrogenation of this tertiary olefin into a diene.

It relates in particular to a process for the production of isoprene from the decomposition of tert-amyl-methyl-ether (TAME) or ethyl-tert-amyl-ether (ETAE) into isoamylenes of high purity that contain 2-methyl-but-1-ene and 2-methyl-but-2-ene, the separation of isoamylenes from methanol or respectively ethanol, and the oxidizing dehydrogenation of these isoamylenes into isoprene (2-methyl-buta-1,3-diene).

The first stage of the process according to the invention is a method for the production of high-purity isoamylenes from an ether, TAME or ETAE whose production makes it possible, for example, to upgrade an olefinic fraction with five carbon atoms that contains at least one 2-methylbutene, such as the one that is produced by the catalytic cracking on the moving bed (called F.C.C, whose initials come from the English "Fluid Catalytic Cracking"), steam cracking, the dehydrogenation of isopentane or isomerization of olefins with five carbon atoms. Their synthesis results from the selective addition of methanol, or ethanol on isoamylenes (2-methyl-but-1-ene and 2-methyl-but-2-ene). It involves balanced reactions that can be enhanced within the framework of synthesis of TAME and ETAE as within the framework of their decomposition.

In the latter case, it is possible to obtain, in a selective manner, the isoamylenes with a high purity. This process then makes it possible to prevent the distillation of the isoamylenes of a fraction with five carbon atoms, a difficult process taking into account small differences between the boiling points of the different olefins with five carbon atoms.

By contrast, it is generally easy to separate the TAME or the ETAE from the hydrocarbon fraction from which it is obtained. Once isolated, the ether can be decomposed again to form the initial tertiary olefin and the alcohol that is used. This takes place by an endothermic process in the presence of a generally acid catalyst and at a higher temperature than for the synthesis. The tertiary olefin that is produced can then have high purity based on operating conditions. In a second stage of the process, the tertiary olefin is dehydrogenated to form a diene, preferably isoprene.

The polymerization of the isoprene results in cis-1,4-polyisoprene, an equivalent of natural rubber, which exhibits excellent purity and a homogeneity that is greater than that of natural rubber.

BACKGROUND OF THE INVENTION

It has been shown that isoprene can be produced from a process of three successive stages. U.S. Pat. No. 3,391,214 describes the production of isoprene from isopentane that undergoes a scheme of three reactions (a hydroperoxidation and two epoxidations) in the presence of catalysts that are specific to each stage of the process. The feedstock that is used, however, is isopentane.

The process for decomposition of the tertiary alkyl ethers into tertiary olefins has been known for a long time, as, for example, Patent Application EP-A-0 068 785 shows, and various acidic solids have been described as catalysts of these reactions. Patent Application FR-A-2 291 958 relates to a process for decomposition of TAME or ETAE respectively into isoamylenes and methanol or isoamylenes and ethanol, with use of catalysts that are selected from among the salts, oxides or complexes of tetravalent uranium and can be supported on an alumina-a, for example, that has a Lewis acidity.

International Application WO-A-91/01 804 describes the production of isoamylenes from TAME with a clay catalyst that is treated with an acid that is selected from among hydrofluoric acid, hydrochloric acid and a mixture of hydrofluoric and hydrochloric acids.

U.S. Pat. No. 5,227,564 describes the decomposition of TAME in a vapor phase and in the presence of a catalyst that contains a silica-alumina zeolite, and Patent Application EP-A-0 589 557 and U.S. Pat. No. 4,536,605 describe the use of a catalyst with a calcined silica-alumina base. U.S. Pat. No. 5,171,920 describes the process for obtaining at least one tertiary olefin by decomposition of the corresponding ether, either TAME or ETAE, with a catalyst that consists of silica that is modified by the addition of at least one element, such as Li, Cs, Mg, Ca or La, for example. Such solids are not very active due to the absence of acidity, and they have a mediocre stability over time: the data of Table 1 of Example 13 of said patent indicate that in 800 hours, it is necessary to increase the temperature of 50° C. to keep the ether conversion level constant.

These catalysts that are based on alumina, silica or silica-alumina require the addition of water to improve the recovery of the alcohol and to prevent the secondary reaction of formation of the corresponding dialkyl ether, which is, for example, dimethyl ether (or DME) in the case of the methanol:

$$2MeOH \Leftrightarrow Me-O-Me + H_2O$$

This is described in particular in Patent Applications GB-A-1 165 479 and EP-A-0 589 557. The presence of water, however, lowers the activity of the catalyst by lowering its acidity (see in particular Patent Application GB-A-1 165 479) and can then make it necessary to operate at a higher temperature, which can interfere with the service life of the catalyst. In addition, the presence of water induces an additional secondary reaction: the water reacts with the tertiary olefins to form an alcohol, such as, for example, in the case of isoamylene to form 2-methyl-butan-2-ol. According to this process, therefore, a loss of the tertiary olefin yield is recorded.

Finally, U.S. Pat. No. 5,095,164 describes a process for decomposition of tertiary alkyl ethers such as TAME or ETAE that use ion exchange resins, for example the sulfonated styrene-divinylbenzene resins. It is thus possible to cite the resin Amberlyst 15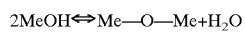(R) of RHOM & HAAS or the resin M-31(R) that is marketed by DOW CHEMICAL. U.S. Pat. No. 4,447,668 also uses an ion exchange resin for producing isoamylenes and diisoamylenes from the separation of TAME.

One of the major drawbacks of the resins that are cited above is the impossibility of using them at high temperature, more specifically above 120° C. Actually, at high temperature, these resins lose sulfonic groups and therefore lose at least in part their activity and/or their acidity. The decomposition reactions of the ethers are endothermic, however; the thermodynamic equilibrium of the reaction is therefore shifted toward olefin production the higher the temperature. An operating temperature that is limited to 120° C. is reflected by weak ether conversion and limited by the laws of thermodynamics.

U.S. Pat. No. 5,095,164 that is cited above uses distillation equipment with a catalyst that is placed at the bottom of a column and that operates between 50 and 100° C., preferably between 60 and 80° C. The thermodynamic equilibrium of the decomposition reaction, which is poorly placed due to the fairly low operating temperature, is shifted by the elimination of the reaction products (tertiary olefin and corresponding alcohol) by distillation. Such a process, however, presents difficulties for the purification of the products. In particular, it uses large amounts of water for the extraction and/or the recovery of the alcohol. In addition, the unconverted ether is recovered at the bottom of the column with significant amounts of alcohol. It should then be purified before being recycled in the process.

The oxidative dehydrogenation of the olefins to form dienes is a process that has been known for a very long time by ones skilled in the art. It is carried out in the presence of catalysts of any type, but that usually contain iron, oxygen and another metallic element. The reaction for oxidizing dehydrogenation of isoamylenes into isoprene is described in, for example, the Encyclopedie Ullmann de Chimie Technique [Ullmann's Encyclopedia of Technical Chemistry], 4th Edition, Volume 13, pages 381–382. Various reaction variants of oxidative dehydrogenation have been proposed.

U.S. Pat. No. 3,156,735 describes the oxidative dehydrogenation of isoamylenes into isoprene, in the presence of a catalyst that contains gold in combination with a noble metal that is selected from the group that consists of platinum, palladium, rhodium, ruthenium and iridium, deposited on a solid refractory oxide substrate that has a small specific surface area.

More recently, U.S. Pat. No. 4,973,793 sets forth the use of a catalyst that is based on iron, oxygen and zinc, in the presence of oxygen and vapor, in the oxidative dehydrogenation reaction of a feedstock that contains isoamylenes and butenes for the production of isoprene. The presence of butenes makes it possible to increase the conversion level of the isoamylenes. This yield decreases, however, if the butene concentration is greater than 80% moles.

SUMMARY OF THE INVENTION

This invention relates to a process for the production of a diene that comprises a decomposition stage a) of at least one tertiary alkyl ether in a mixture that contains at least one tertiary olefin, at least one alcohol and at least one residual ether, in the presence of a catalyst that comprises at least one mineral solid that is grafted by at least one organic group such as alkyl sulfonic acid, aryl sulfonic acid or alkylaryl sulfonic acid, a stage b) for purification of the tertiary olefin that is obtained in stage a) and a stage c) for oxidizing dehydrogenation of the tertiary olefin that is obtained in stage b), in the presence of a catalyst under conditions of obtaining a diene.

DETAILED DESCRIPTION OF THE INVENTION

In the first stage of the process according to the invention, the tertiary alkyl ether is decomposed into a tertiary olefin of high purity, in the presence of a catalyst that comprises at least one mineral solid, for example of polysiloxane type, grafted by at least one organic group such as alkyl sulfonic acid that usually contains from 1 to 24 carbon atoms, preferably 2 to 20 and even more preferably from 2 to 5 carbon atoms, aryl sulfonic acid that usually contains from 6 to 18 carbon atoms, or alkylaryl sulfonic acid that usually contains from 7 to 24 carbon atoms. More particularly, the tertiary alkyl ether is TAME or ETAE that decomposes into isoamylenes that are 2-methyl but-1-ene and 2-methyl but-2-ene (whereby the 3-methyl but-1-ene is not very reactive) and into the corresponding alcohols (methanol or ethanol).

Said catalyst that preferably comprises a solid such as polysiloxane that is grafted by at least one organic group is in particular marketed under the registered trademark "DELOXAN", which contains a polymeric unit of the formula:

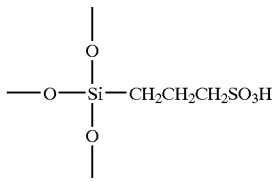

The preparation of such a solid is described in, for example, Patents U.S. Pat. No. 4,552,700, U.S. Pat. No. 5,354,831 and U.S. Pat. No. 5,380,791. These solids have a strong Brönsted acidity. The possibility of using such solids in ether decomposition reactions is mentioned in, for example, Patent FR-B-2 747 120.

These catalysts are very active for the decomposition reaction of tertiary alkyl ethers into the corresponding tertiary olefins. They make it possible to operate at a low temperature, for example at 130° C., which promotes good stability of the catalyst and can also be reflected by a very long service life of the catalyst. If the endothermicity of the reaction is also taken into account, and therefore the favorable shifting of the thermodynamic equilibrium by a temperature elevation, it is possible to work, with these catalysts, at high temperature (typically, for example, above 150° C. and often between 180° C. and 220° C.)

The fact that the grafted solid is mineral and non-organic, for example such as polysiloxane, makes it possible to work at such temperatures without noteworthy degradation of the catalyst. In the case of use of high temperatures in the first stage of the process according to the invention, the strong activity of the catalysts that are used according to the process of this invention makes it possible to work with high L.H.S.V. (hourly liquid volumetric flow rate, expressed in volume of liquid feedstock per volume of catalyst and per hour). This is reflected by the reduction of the necessary catalytic volume and also by the reduction of installation equipment (hence a double economic advantage). In addition, the possibility of working with high traverse speeds (high L.H.S.V.) reduces the part of secondary reactions; very good yields of tertiary olefins and alcohol are ultimately obtained.

The catalyst that is used in stage a) of this invention has excellent stability over time for the decomposition reaction, which facilitates the operations and offers a certain economic advantage, based on improvements such as less frequent rest periods and an overall savings on the cost of the catalysts.

The operating conditions for the decomposition stage of the tertiary alkyl ether are as follows. The (relative) pressure is generally between 0.1 to 3 MPa, preferably between 0.1 and 1 MPa. The temperature is from 100 to 230° C., preferably between 120 and 200° C., and the hourly volumetric flow rate per volume of catalyst per hour (L.H.S.V.) is from 1 to 200 $h^{-1}$, often between 1 to 100 $h^{-1}$. Thus, it is preferred to work between 120 and 200° C. with a L.H.S.V. of about 2 to 50 and preferably about 2 to 20. The selection of the pair of parameters (temperature, L.H.S.V.) is essential for optimizing the performance levels of the catalyst (optimum conversion of the TAME and good selectivities of alcohol and isoamylenes, i.e., considerably limited secondary reactions).

Stage b) of the process according to the invention is a purification of the tertiary olefin that is obtained in stage a) for extracting said olefin from the mixture that is obtained from stage a). The purification comprises at least one stage, most often two stages. By way of example, the purification can comprise at least one water washing stage and at least one distillation stage, whereby the washing and the distillation are carried out in any order. The washing is preferably carried out before the distillation.

The operating conditions of the washing with water of stage b) for purification of the olefin comprise an amount of water such that the volumetric ratio between the water volume and the volume of the mixture that is obtained in stage a) is usually from about 0.005 to 100, most often from about 0.01 to 20, preferably from about 0.1 to 10 and even more preferably from about 0.5 to 5. This washing most often uses a plate column that operates at a temperature from about 1 to 100° C., preferably from about 10 to 60° C. The absolute pressure is generally from about 0.1 to 2 MPa, most often from about 0.1 to 1.5 MPa.

The operating conditions of the distillation of stage b) for purification of the olefin comprise a pressure in the distillation column that is usually from about 0.1 to 1.5 MPa, preferably from about 0.2 to 1 MPa, identical or different to that of the washing. The distillation column usually comprises between 3 and 80 theoretical plates and most often between 10 and 50 theoretical plates.

The mixture that is obtained in stage a) contains at least one tertiary olefin, at least one alcohol and at least one residual ether. In the case where the washing is carried out before distillation, the washing stage makes it possible to collect a tertiary olefin-rich organic phase that contains olefin and at least a portion of the residual ether, and an alcohol-rich aqueous phase. The organic phase is then distilled. The tertiary olefin comes out at the top of the column, and the residual ether comes out at the bottom of the column.

The alcohol-rich aqueous phase is treated, preferably by distillation, to recycle water to purification stage b) and to recover the alcohol that is obtained in stage a). The synthesis of a tertiary alkyl ether, such as TAME or ETAE, can come from the reaction of an olefinic fraction with five carbon atoms that is produced by the catalytic cracking on a moving bed (FCC), steam cracking, dehydrogenation of isopentane or isomerization of branched olefins with five carbon atoms, with an alcohol. This alcohol can come in part from the alcohol-rich aqueous phase and is obtained in stage b) after the water is separated from the water of said phase.

In the case where the distillation is carried out before the washing, the distillation stage of the mixture that is formed in stage a) makes it possible to collect at the top of the column a tertiary olefin-rich organic phase that contains olefin and a portion of alcohol. At the bottom of the column, an ether-enriched organic phase that contains another portion of the alcohol is recovered. The organic phase is then washed with water to purify the olefin. The flows that contain alcohol can be, after optional purification treatments, sent at least in part to a unit for ether synthesis. The water that is obtained from the washing is advantageously recycled to purification stage b).

In the case of the synthesis of TAME, the alcohol that reacts with the olefinic fraction with five carbon atoms is the methanol. In the ETAE case, it is ethanol.

The tertiary olefin, preferably an isoamylene or a mixture of isoamylenes, that is obtained at the end of the second stage of the process according to the invention is dehydrogenated, in gas phase and in the presence of a catalyst, to form a diene, preferably isoprene.

Although the catalyst that is used in the dehydrogenation stage can be any type of catalyst that is able to carry out the dehydrogenation reaction, a catalyst that is resistant to the deposition of coke is preferably used to obtain improved selectivity and activity of the catalyst. The most used catalysts have a metal oxide base such as Co, Ni, Mo and W, and an alkaline metal oxide, generally on substrates of alumina, silica or silica-alumina. In a preferred form of the process according to the invention, a catalyst that consists of nickel oxide, molybdenum oxide and potassium oxide that are supported on an alumina-γ is used.

The operating conditions for the oxidizing dehydrogenation stage comprise a (partial) hydrocarbon pressure that is usually from about $10^4$ to $5.10^5$ Pa, preferably between about $10^4$ to $2.10^5$ Pa. The temperature is generally between about 450 and 700° C., preferably between about 600 and 680° C. The feedstock weight/catalyst weight/hour (H.W.V.=hourly weight velocity) is usually between about 0.1 and 5 $h^{-1}$, preferably between about 0.5 and 2 $h^{-1}$.

The entire disclosure of all applications, patents and publications, cited above and below, and of corresponding French application 98/11285, filed Sep. 9, 1998, are hereby incorporated by reference.

The following example illustrates the invention, without limiting its scope:

EXAMPLE 6 g of DELOXAN ASP$^{(R)}$ catalyst is introduced into a tubular reactor with a useful volume that is equal to 50 cm$^3$. This reactor is equipped with a double jacket, in which circulates a coolant that ensures the thermal regulation. The actual temperature is determined with a thermocouple that is placed in a sheath that traverses the reactor from one side to the other. The shifting of the thermocouple within the sheath makes it possible to know the temperature gradient inside the reactor. The pressure of the system is maintained downstream with a reducing valve that is calibrated to $7.10^5$ relative Pa. The effluent is analyzed regularly thanks to a line chromatograph that is equipped with a flame ionization detector.

The feedstock consists of 94% TAME and circulates from the top to the bottom of a reactor ("down-flow" direction).

The results that are obtained during tests that use different temperature-L.H.S.V. pairs are summarized in the following table:

| Test No. | T Regulation (° C.) | T Output (° C.) | LHSV ($h^{-1}$) | $\alpha_{TAME}$ (%) | $S_{MeOH}$ (%) | $S_{isoamylenes}$ (%) |
|---|---|---|---|---|---|---|
| 1 | 120 | 117.7 | 6 | 47.5 | 99.2 | 99.3 |
| 2 | 140 | 121.8 | 6 | 84.3 | 99.0 | 99.8 |

-continued

| Test No. | T Regulation (° C.) | T Output (° C.) | LHSV (h$^{-1}$) | $\alpha_{TAME}$ (%) | $S_{MeOH}$ (%) | $S_{isoamylenes}$ (%) |
|---|---|---|---|---|---|---|
| 3 | 160 | 141.4 | 6 | 94.6 | 98.2 | 99.6 |
| 4 | 140 | 119.0 | 12 | 57.3 | 99.3 | 99.6 |
| 5 | 150 | 121.8 | 12 | 67.3 | 99.4 | 99.8 |

In this table, $\alpha_{TAME}$ is the conversion of TAME, and $S_{MeOH}$ and $S_{isoamylenes}$ are respectively the selectivities of methanol and isoamylenes relative to converted TAME.

It is seen that the selectivities of isoamylenes and alcohol are very high, which indicates that the secondary reactions are considerably limited.

The effluents that are obtained in each of the tests that are described above are mixtures of isoamylenes, methanol and unconverted ether (TAME). The purification of the isoamylenes comprises washing with water followed by a distillation.

The mixture that is obtained in test no. 3 is used below.

The washing of the mixture uses an amount of water such that the volumetric ratio between the volume of water and the volume of the mixture is equal to 1. This washing uses an ampoule that is to be decanted. It is carried out at 20° C., at atmospheric pressure. After washing, an isoamylene-rich organic phase that contains isoamylenes and residual ethers and a methanol-rich aqueous phase are collected. A distillation of the organic phase is then carried out at the pressure of about 0.1 MPa. The distillation column comprises 10 theoretical plates.

The dehydrogenation reaction of the isoamylenes took place in a gas phase, in the presence of a catalyst that is based on nickel oxide, molybdenum oxide, and potassium oxide that is supported on an alumina-γ and that contains 5.60% by weight of NiO, 15.10% by weight of MoO and 6.60% by weight of $K_2O$.

150 g of said catalyst is introduced into a tubular reactor. The isoamylenes that are obtained after purification are introduced by keeping the temperature of the reactor at 650° C., and the H.W.V. is 1.2 h$^{-1}$ and the (partial) hydrocarbon pressure is $10^5$ Pa. The liquid effluent at the outlet of the reactor is regularly analyzed by gas phase chromatography. The conversion of the isoamylenes in a single pass is 70%, with an isoprene selectivity of 68%.

The preceding example can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A process for the production of isoprene from an olefinic cut with five carbon atoms in four stages, comprising:

etherification of an olefinic cut with five carbon atoms in the presence of methanol or ethanol under etherification conditions to produce tert-amyl-methyl-ether (TAME) or ethyl-tert-amyl-ether (ETAE);

decomposition of said TAME or ETAE to a mixture containing isoamylenes, methanol or ethanol and any residual ether, in the presence of a catalyst comprising at least one mineral solid grafted by at least one organic group of an alkyl sulfonic acid, an aryl sulfonic acid or an alkylaryl sulfonic acid;

purification of said isoamylenes; and oxidative dehydrogenation of the isoamylenes in the presence of a catalyst under conditions for obtaining isoprene.

2. A process according to claim 1 in which, in said etherification, said TAME or ETAE is obtained from the reaction of said methanol or ethanol with an olefinic cut with five carbon atoms produced by fluid catalytic cracking, or by steam cracking.

3. A process according to claim 1, in which said mineral solid that is contained in the catalyst of said decomposition is a polysiloxane.

4. A process according to claim 1, in which said mineral solid that is contained in the catalyst of said decomposition is grafted by at least one alkyl sulfonic acid.

5. A process according to claim 4, wherein said at least one alkyl sulfonic acid contains 2 to 20 carbon atoms.

6. A process according to claim 5, wherein said at least one alkyl sulfonic acid contains 2 to 5 carbon atoms.

7. A process according to claim 1, in which the operating conditions of said decomposition comprise a relative pressure of between 0.1 to 3 MPa, a temperature of between 100 and 230° C., and an hourly volumetric flow rate per volume of catalyst and per hour that is between 1 and 200 h$^{-1}$.

8. A process according to claim 7, wherein the relative pressure for the decomposition stage is 0.1–1.0 MPa.

9. A process according to claim 7, wherein the temperature for the decomposition stage is 120–200° C.

10. A process according to claim 9, wherein L.S.H.V. for the decomposition stage is about 2–50.

11. A process according to claim 9, wherein L.S.H.V. for the decomposition stage is about 2–20.

12. A process according to claim 7, wherein the hourly volumetric flow rate per volume of catalyst and per hour for the decomposition stage is 1–100 h$^{-1}$.

13. A process according to claim 1, in which the purification of the isoamylenes comprises at least one washing with water and at least one distillation, whereby the washing and the distillation are carried out in any order.

14. A process according to claim 13, wherein the operating conditions of the washing with water in said purification comprise the use of water in a volumetric ratio with the mixture that is obtained in said decomposition from about 0.005 to 100, a temperature from about 1 to 100° C. and an absolute pressure from about 0.1 to 2 MPa, and the operating conditions of the distillation in said purification comprise a pressure in the distillation column from about 0.1 to 1.5 MPa, identical to or different from that of the washing, whereby said column comprises a number of plates of between 3 and 80 theoretical plates.

15. A process according to claim 14, wherein the volumetric ratio for the washing with water is about 0.01–20.

16. A process according to claim 14, wherein the volumetric ratio for the washing with water is about 0.1–10.

17. A process according to claim 14, wherein the volumetric ratio for the washing with water is about 0.5–5.

18. A process according to claim 14, wherein the temperature of a plate column is 10–60° C.

19. A process according to claim 14, wherein the absolute pressure for the washing with water is about 0.1–1.5 MPa.

20. A process according to claim 14, wherein the pressure in the distillation column for the washing with water is 0.2–1 MPa and the number of theoretical plates is 10–50.

21. A process according to claim 1, in which the purification of the isoamylenes comprises a washing with water of the mixture that is obtained from said decomposition so as to obtain an isoamylene-rich organic phase that contains isoamylene, unconverted TAME or ETAE and a methanol- or an ethanol-rich aqueous phase, followed by the distillation of the organic phase to recover the isoamylene and the unconverted TAME or ETAE.

22. A process according to claim 21, in which the water of the methanol or ethanol-rich aqueous phase that is obtained from said purification is separated from methanol or ethanol and then recycled to said purification.

23. A process according to claim 1, in which the catalyst of said oxidative dehydrogenation comprises at least one metal oxide of Co, Ni, Mo, W or an alkaline metal, on a substrate of alumina, silica or silica-alumina.

24. A process according to claim 1, which the operating conditions of said oxidative dehydration comprise a partial hydrocarbon pressure of between $10^4$ and $5.10^5$ Pa, a temperature of between 450 and 700° C. and a feedstock weight/catalyst weight/hour of between 0.1 and 5 $h^{-1}$.

25. A process according to claim 24, in which the catalyst of said oxidative dehydrogenation consists essentially of at least one metal oxide of Co, Ni, Mo, W or an alkaline metal, on a substrate of alumina, silica or silica-alumina.

26. A process according to claim 24, in which the catalyst of said oxidative dehydrogenation consists of at least one metal oxide of Co, Ni, Mo, W or an alkaline metal, on a substrate of alumina, silica or silica-alumina.

27. A process according to claim 1, wherein the isoprene is obtained by converting at least about 70% of the isoamylenes in a single pass with a selectivity of isoprene of at least about 68%.

28. A process according to claim 1, in which the operating conditions of said decomposition comprise a relative pressure of between 0.1–1 MPa, a temperature of 120–200° C., and an hourly volumetric flow rate per volume of catalyst and per hour that is 2–50 $h^{-1}$.

29. A process according to claim 1, in which the operating conditions of said oxidative dehydrogenation comprise a partial hydrocarbon pressure of $10^4$–$2.10^5$ Pa, a temperature of 600–680° C. and a feedstock weight/catalyst weight/hour of 0.5–2 $h^{-1}$.

30. A process according to claim 1, wherein said organic group is an alkyl sulfonic acid containing 1 to 24 carbon atoms, an aryl sulfonic acid containing 6 to 18 carbon atoms, or an alkylaryl sulfonic acid containing 7 to 24 carbon atoms.

31. A process for the production of isoprene from an olefinic cut with five carbon atoms in four stages, comprising:

etherification of an olefinic cut with five carbon atoms in the presence of methanol or ethanol under etherification conditions to produce tert-amyl-methyl-ether (TAME) or ethyl-tert-amyl-ether (ETAE);

decomposition of said TAME or ETAB to a mixture containing isoamylenes, methanol or ethanol and any residual ether, in the presence of a catalyst comprising at least one mineral solid grafted by at least one organic group of an alkyl sulfonic acid, an aryl sulfonic acid or an alkylaryl sulfonic acid wherein said mineral solid that is contained in the catalyst of said decomposition is grafted by at least one alkyl sulfonic acid and the catalyst of said decomposition comprises at least one unit of formula (I) below:

$(O_{3/2}Si\text{-}R^1\text{-}SO_3^-)H^+$ (I)

where $R^1$ is an alkyl radical;

purification of said isoamylenes; and oxidative dehydrogenation of the isoamylenes in the presence of a catalyst under conditions for obtaining isoprene.

32. A process for the production of isoprene from an olefinic cut with five carbon atoms in four stages, comprising:

etherification of an olefinic cut with five carbon atoms in the presence of methanol or ethanol under etherification conditions to produce tert-amyl-methyl-ether (TAME) or ethyl-tert-amyl-ether (ETAE);

decomposition of said TAME or ETAE to a mixture containing isoamylenes, methanol or ethanol and any residual ether, in the presence of a catalyst comprising at least one mineral solid grafted by at least one organic group of an alkyl sulfonic acid, an aryl sulfonic acid or an alkylaryl sulfonic acid wherein said mineral solid that is contained in the catalyst of said decomposition is grafted by at least one alkyl sulfonic acid and in which said catalyst of said decomposition contains a polymeric unit of the formula:

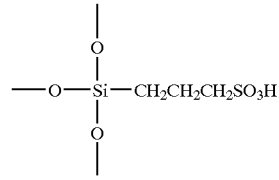

purification of said isoamylenes; and oxidative dehydrogenation of the isoamylenes in the presence of a catalyst under conditions for obtaining isoprene.

33. A process for the production of isoprene from an olefinic cut with five carbon atoms in four stages, comprising:

etherification of an olefinic cut with five carbon atoms in the presence of methanol or ethanol under etherification conditions to produce tert-amyl-methyl-ether (TAME) or ethyl-tert-amyl-ether (ETAB);

decomposition of said TAME or ETAE to a mixture containing isoamylenes, methanol or ethanol and any residual ether, in the presence of a catalyst comprising at least one mineral solid grafted by at least one organic group of an alkyl sulfonic acid, an aryl sulfonic acid or an alkylaryl sulfonic acid;

purification of said isoamylenes; and oxidative dehydrogenation of the isoamylenes in the presence of a catalyst comprising at least one metal oxide of Co, Ni, Mo, W or an alkali metal, on a substrate of alumina, silica or silica-alumina under conditions comprising a partial hydrocarbon pressure of between $10^4$ and $5.10^5$ Pa, a temperature of between 450 and 700° C. and a feedstock weight/catalyst weight/hour of between 0.1 and 5 $h^{-1}$ for obtaining isoprene.

34. A process for the production of isoprene from an olefinic cut with five carbon atoms in four stages, comprising:

etherification of an olefinic cut with five carbon atoms in the presence of methanol or ethanol under etherification conditions to produce tert-amyl-methyl-ether (TAME) or ethyl-tert-amyl-ether (ETAE) wherein said TAME or ETAE is obtained from the reaction of said methanol or ethanol with an olefinic cut with five carbon atoms produced by fluid catalytic cracking or by steam cracking;

decomposition of said TAME or ETAE to a mixture containing isoamylenes, methanol or ethanol and any residual ether, in the presence of a catalyst comprising at least one mineral solid grafted by at least one organic group of an alkyl sulfonic acid, an aryl sulfonic acid or an alkylaryl sulfonic acid wherein the operating conditions of said decomposition comprise a relative pressure of between 0.1 to 3 MPa, a temperature of between 100 and 230° C., and an hourly volumetric flow rate per volume of catalyst and per hour that is between 1 and 200 $h^{-1}$;

purification of said isoamylenes; in which the purification of the isoamylenes comprises at least one washing with water and at least one distillation, whereby the washing and the distillation are carried out in any order, and wherein the operating conditions of the washing with water in said purification comprise the use of water in a volumetric ratio with the mixture that is obtained in said decomposition from about 0.005 to 100, a temperature from about 1 to 100° C. and an absolute pressure from about 0.1 to 2 MPa, and the operating conditions of the distillation in said purification comprise a pressure in the distillation column from about 0.1 to 1.5 MPa, identical to or different from that of the washing, whereby said column comprises a number of plates of between 3 and 80 theoretical plates, and oxidative dehydrogenation of the isoamylenes in the presence of a catalyst comprising at least one metal oxide of Co, Ni, Mo, W or an alkaline metal, on a substrate of alumina, silica or silica-alumina under conditions comprising a partial hydrocarbon pressure of between $10^4$ and $5.10^5$ Pa, a temperature of between 450 and 700° C. and a feedstock weight/catalyst weight/hour of between 0.1 and 5 $h^{-1}$ for obtaining isoprene.

\* \* \* \* \*

UNITED STATES PATENT AND TRADEMARK OFFICE
CERTIFICATE OF CORRECTION

PATENT NO.     : 6,667,423 B2                                              Page 1 of 1
DATED          : December 23, 2003
INVENTOR(S)    : Claire Dumonteil et al.

It is certified that error appears in the above-identified patent and that said Letters Patent is hereby corrected as shown below:

<u>Column 9,</u>
Line 56, reads "ETAB" should read -- ETAE --

<u>Column 10,</u>
Line 43, reads "(ETAB)" should read -- (ETAE) --

Signed and Sealed this

Seventh Day of September, 2004

JON W. DUDAS
*Director of the United States Patent and Trademark Office*